United States Patent [19]
Cairns et al.

[11] 3,948,954
[45] Apr. 6, 1976

[54] BIS-CHROMONE-TETRAZOLE/HYDROXAMIC/CARBOXYLIC ACIDS

[75] Inventors: Hugh Cairns; Norman Harold Rogers, both of Loughborough, England

[73] Assignee: Fisons Limited, England

[22] Filed: Jan. 21, 1974

[21] Appl. No.: 435,008

[30] Foreign Application Priority Data
Jan. 19, 1973 United Kingdom.............. 2862/73

[52] U.S. Cl. ...... 260/345.2; 260/308 D; 260/345.5; 424/269; 424/283
[51] Int. Cl.² ..................................... C07D 311/02
[58] Field of Search.......... 260/345.2, 345.5, 308 D

[56] References Cited
UNITED STATES PATENTS
| | | | |
|---|---|---|---|
| 3,419,578 | 12/1968 | Fitzmaurice et al. | 260/345.2 |
| 3,484,445 | 12/1969 | Lee et al. | 260/345.2 |
| 3,629,290 | 12/1971 | Cairns et al. | 260/345.2 |
| 3,790,580 | 2/1974 | Johnson et al. | 260/345.2 |
| 3,823,165 | 7/1974 | Cairns et al. | 260/345.2 |
| 3,857,856 | 12/1974 | Cairns et al. | 260/345.2 |

*Primary Examiner*—James O. Thomas, Jr.
*Assistant Examiner*—Nicky Chan
*Attorney, Agent, or Firm*—Wenderoth, Lind & Ponack

[57] ABSTRACT
There are described compounds of formula I,

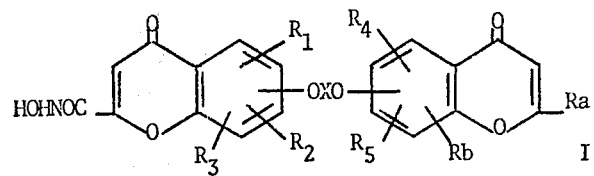

in which
$R_1$, $R_2$, $R_3$, $R_4$, $R_5$ and $R_6$, which may be the same or different, each represent hydrogen, halogen, hydroxy, alkyl C1 to 6, alkoxy C1 to 6, alkenyl C1 to 6; the alkyl and alkoxy groups optionally being substituted by hydroxy, alkoxy C1 to 6, halogen or phenyl, and X is a hydrocarbon group containing from 2 to 10 carbon atoms, which is optionally interrupted by an oxygen atom, and/or substituted by an -OH group, Ra is a group -COOH, or

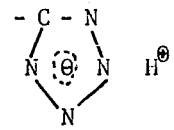

and pharmaceutically acceptable derivatives thereof.

There are also described methods of making the compounds and pharmaceutical, e.g. anti-allergic, compositions containing them.

10 Claims, No Drawings

BIS-CHROMONE-TETRAZOLE/HYDROXAMIC/-CARBOXYLIC ACIDS

This invention relates to new compounds, compositions containing them and methods for their preparation.

According to our invention we provide a compound of formula I,

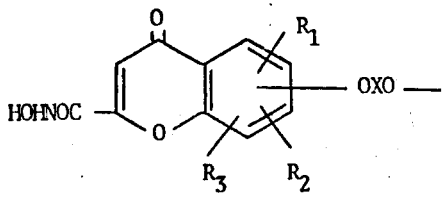

— OXO —

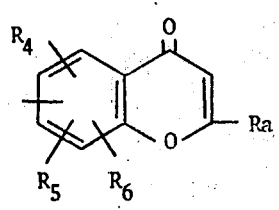   I in which $R_1$, $R_2$, $R_3$, $R_4$, $R_5$ and $R_6$, which may be the same or different, each represent hydrogen, halogen, hydroxy, alkyl C1 to 6, alkoxy C1 to 6, alkenyl C1 to 6; the alkyl and alkoxy groups optionally being substituted by hydroxy, alkoxy C1 to 6, halogen or phenyl, and X is a hydrocarbon group containing from 2 to 10 carbon atoms, which is optionally interrupted by an oxygen atom, and/or substituted by an -OH group, Ra is a group -COOH, or

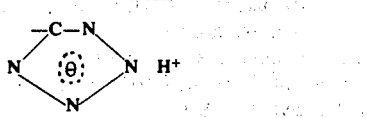

and pharmaceutically acceptable derivatives thereof.

According to the invention we also provide a process for the production of a compound of formula I, or a pharmaceutically acceptable derivative thereof, which comprises a. reacting a compound of formula VI,

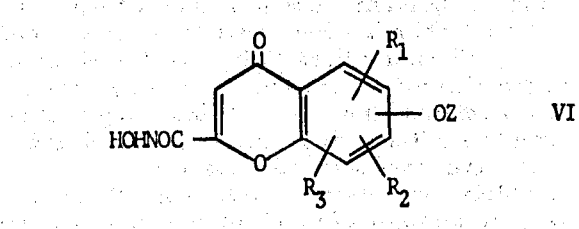   VI with a compound of formula VII,

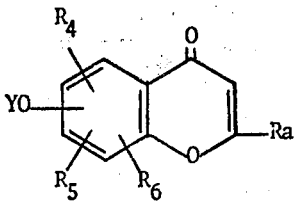   VII or an ester thereof, in which formulae $R_1$, $R_2$, $R_3$, $R_4$, $R_5$, $R_6$ and Ra are as defined above, and Y represents hydrogen or a reactive metal when Z represents a group Xbb, and when X represents hydrogen or a reactive metal Y represents a group Xb, and Xb represents a hydrocarbon group, containing from 2 to 10 carbon atoms which is optionally interrupted by an oxygen atom and carrying an epoxide group or an anion forming group, which upon reaction with hydrogen or a reactive metal yields a group X, b. producing a compound of formula Ib,

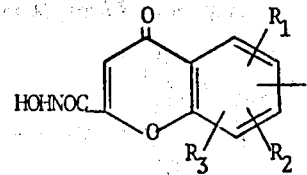

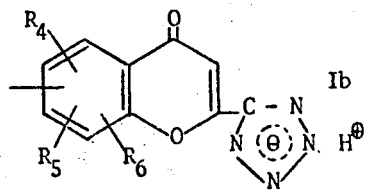   Ib in which $R_1$, $R_2$, $R_3$, $R_4$, $R_5$, $R_6$ and X are as defined above, by i. reacting a compound of formula VIII,

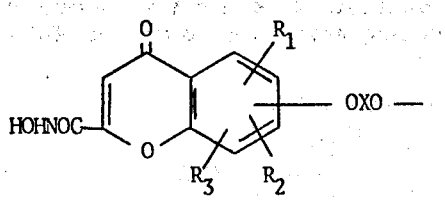   — OXO —

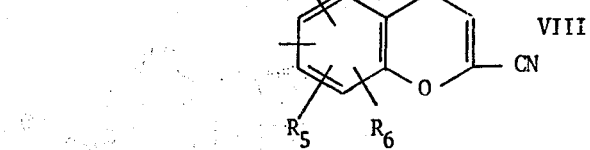   VIII in which $R_1$, $R_2$, $R_3$, $R_4$, $R_5$, $R_6$ and X are as defined above, with an azide in a solvent which is inert under the reaction conditions, or ii. removing a group $R_{11}$ from a compound of formula III or IV,

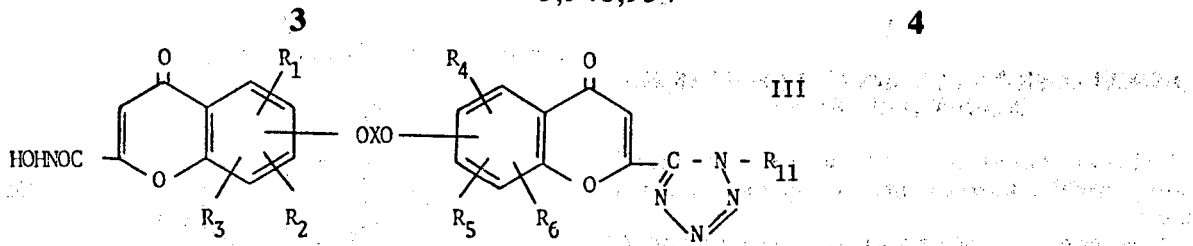

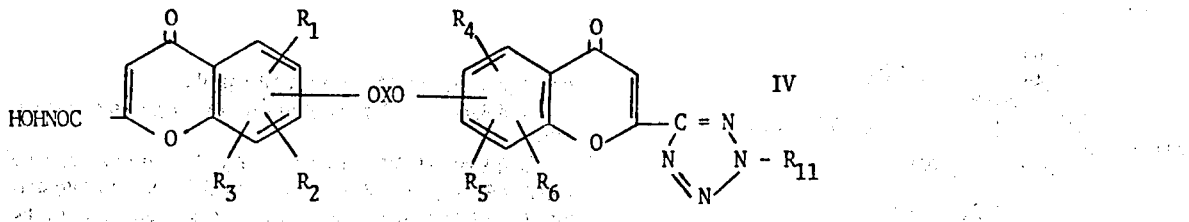

in which formulae III and IV
$R_1$, $R_2$, $R_3$, $R_4$, $R_5$, $R_6$ and X are as defined above, and $R_{11}$ represents a group which may be replaced by hydrogen, c. producing a compound of formula Ia,

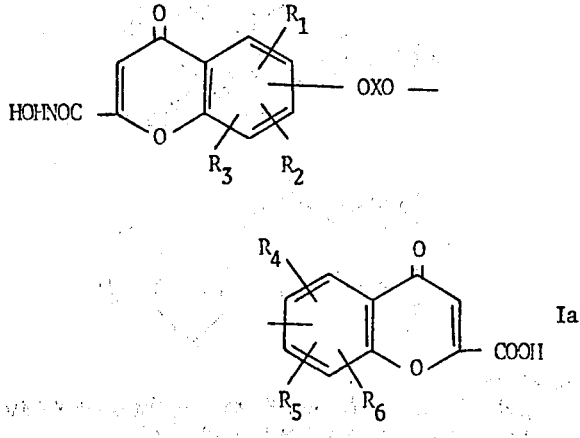

in which $R_1$, $R_2$, $R_3$, $R_4$, $R_5$, $R_6$ and X are as defined above, by selectively hydrolysing a compound of formula IX,

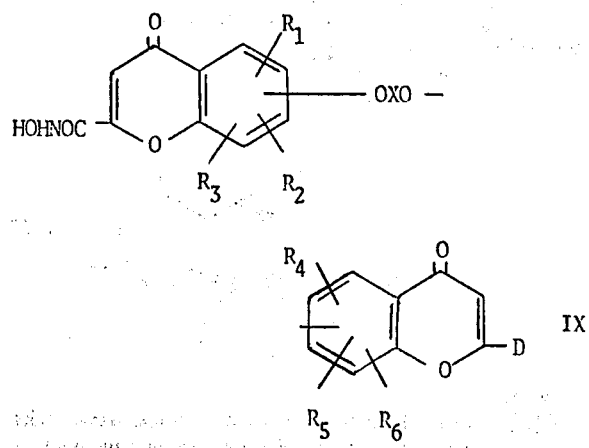

in which
$R_1$, $R_2$, $R_3$, $R_4$, $R_5$, $R_6$ and X are as defined above, and
D represents a group hydrolyseable to a —COOH group, or d. reacting a mono- ester, -anhydride or -acid halide of a compound of formula X, in which
$R_1$, $R_2$, $R_3$, $R_4$, $R_5$, $R_6$, Ra and X are as defined above, with hydroxylamine, and where desired or necessary converting the compound of formula I to a pharmaceutically acceptable derivative thereof.

In process (a) when Y or Z is a reactive metal the metal may be, for example, an alkali metal, e.g. sodium or another reactive metal, e.g. thallium. When Y or Z represents a group Xb carrying an anion forming group the anion forming group may be, for example, a halogen atom, e.g. bromine, or a sulphonate group, e.g. a methylsulphonate or a p-toluenesulphonate group. When Y or Z represents a group Xb carrying a halogen atom the reaction may be carried out in the presence of a solvent which is inert under the reaction conditions, e.g. acetone and in the presence of an acid acceptor, e.g. potassium carbonate. The reaction is also preferably carried out under anhydrous conditions and in the presence of a suitable catalyst, e.g. KI. When Y or Z represent a group Xb carrying an epoxide group the reaction may be carried out at an elevated temperature in a solvent which is inert under the reaction conditions, e.g. dioxan or dimethylformamide, and in the presence of a suitable catalyst, e.g. trimethylbenzylammonium hydroxide. It may be necessary to protect the groups Ra and Rb during the reaction and to remove the protecting group after the reaction.

Suitable solvents which are inert under the reaction conditions of process (b) (i) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130°C for from about 1 to 20 hours. The azide used in the reaction is preferably ammonium or an alkali metal azide, e.g. sodium or lithium azide but other azides, e.g. aluminium azide or the azides of nitrogen containing bases, e.g. mono- di- tri- and tetra- methylammonium, anilinium, morpholinium and piperidinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above the reaction may be carried out using hydrazoic acid (hydrogen azide) at a temperature of from about 20° to 150°C in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid.

In process $(b)(ii)$ the group $R_{11}$ may be, for example, an aralkyl, e.g. a benzyl, p-methoxybenzyl, triphenylmethyl or diphenylmethyl group; an aroylalkyl, e.g. a phenacyl group; an acyl, e.g. acetyl group; an amino group; or a group $-(CH_2)_2G$, where G is an electron withdrawing group, for example a nitrile, a carboxylic ester, e.g. of a lower alkanol, or an acyl group, e.g. an acetyl group.

When $R_{11}$ represents an aralkyl group the group may be removed either using a hydrogen halide, e.g. HBr in acetic acid or by catalytic hydrogenation using, for example, a palladium catalyst in a solvent which is inert under the reaction conditions, e.g. acetic acid, or by using sodium in liquid ammonia.

When $R_{11}$ represents an acyl group or a group $-CH_2CH_2G$, the group may be removed under basic conditions with, for example, sodium hydroxide.

When $R_{11}$ represents an amino group, the group may be removed by reductive de-amination with, for example, hypophosphorous acid, stannous chloride or sodium in liquid ammonia.

In process $(c)$ the D group may be, for example an ester, e.g. an ester derived from a C1 to 10 alkanol, a nitrile group or a simple amide group, e.g. derived from ammonia or a C1 to 6 mono- or di-alkyl amine. The hydrolysis may be carried out using conventional techniques, for example under mildly basic conditions, e.g. using sodium bicarbonate or sodium carbonate, or under acidic conditions, e.g. using a mixture of aqueous dioxan and hydrochloric acid, or hydrogen bromide in acetic acid In process (d) the anhydride is preferably a mixed annydride of such a type that it will cleave preferentially, to give the desired benzopyran -carbohydroxamic acid, as the major product when reacted with hydroxylamine. Examples of suitable acids from which the mixed anhydride may be derived are sulphonic acids, e.g. benzene sulphonic acid, sterically hindered carboxylic acids, e.g. pivalic, isovaleric, diethylacetic or triphenylacetic acid, and alkoxy formic acids, e.g. ethoxy or isobutoxy formic acid. The reaction is preferably carried out under anhydrous conditions in a solvent which will not react with either the hydroxylamine or the mixed anhydride e.g. pyridine or dimethylformamide. However when the reaction is carried out in a non-basic solvent, e.g. dimethylformamide, an adequate proportion of an acid acceptor, e.g. triethylamine, should also preferably be present. The reaction is preferably carried out at a temperature of from about $-15°$ to $+20°C$. When an acid halide is used it may conveniently be an acid chloride. Suitable esters include those derived from alkanols containing from 1 to 10 and preferably from 1 to 6 carbon atoms. When an ester is used the reaction may conveniently be carried out in a solvent which is inert under the reaction conditions, e.g. dimethylformamide, water or a mixture thereof, in the presence of a base, e.g. sodium hydroxide, and at room temperature, i.e. at about 20°C.

Compounds of formula VI, VII, IX and X are either known or may be made from known starting materials using conventional techniques.

Compounds of formula III and IV may be made by reacting a compound of formula V,

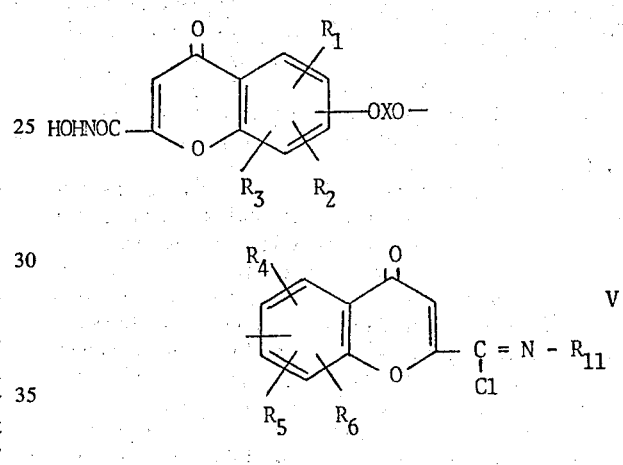

in which $R_1$, $R_2$, $R_3$, $R_4$, $R_5$, $R_6$, $R_{11}$ and X are as defined above, with an azide. The reaction may be carried out under substantially the the same conditions as set out above for process$(b)$ $(i)$ The compounds of formula V may be made by reacting a corresponding compound in which the group $-C(Cl)=N-R_{11}$ is replaced by a group $-CONH-R_{11}$ with phosphorus pentachloride.

The compounds of formulae III and IV may also be made from compounds of formula Ib using techniques known per se, for example by reacting with a compound $R_{11}$ Hal, in which $R_{11}$ is as defined above and Hal represents a halogen atom. Compounds of formulae III and IV in which $R_{11}$ is an amino group may be made by reacting a compound of formula Ib with hydroxylamino—O—sulphonic acid in weakly alkaline aqueous solution, and compounds of formulae III and IV in which $R_{11}$ represents a group $CH_2CH_2G$ may also be made by Michael addition of a compound $-CH_2=CHG$ to a compounds of formula Ib Compounds of formula I may be isolated from their reaction mixtures using conventional techniques.

The process described above may produce the compound of formula I or a derivative thereof. It is also within the scope of this invention to treat any derivative so produced to liberate the free compound of formula I, or to convert one derivative into another. Suitable derivatives include salts and notably water-soluble salts. Salts which may be mentioned include basic addition salts, e.g. alkali-metal and alkaline-earth metal salts, notably the sodium salt.

The compounds of formula I, and pharmaceutically acceptable derivatives thereof, are useful because they possess pharmacological activity in animals; in particular they are useful because they inhibit the release and/or action of pharmacological mediators which result from the in vivo combination of certain types of antibody and specific antigen, e.g. the combination of reaginic antibody and specific antigen. (See Example A below).

In man, both subjective and objective changes which result from the inhalation of specific antigen by sensitised subjects are inhibited by prior administration of the new compounds. Thus the new compounds are indicated for use in the treatment of asthma, e.g. allergic asthma. The new compounds are also indicated for use in the treatment of so-called 'intrinsic' asthma (in which no sensitivity to extrinsic antigen can be demonstrated). The new compounds may also be of value in the treatment of other conditions in which antigen-antibody reactions are responsible for disease, for example, allergic rhinitis; certain eye conditions, e.g. trachoma; urticaria; gastrointestinal allergy, especially in children, e.g. milk allergy; and other disorders of the gastrointestinal tract and oro-pharynx which have an immunological component.

For the above mentioned uses the dosage administered will, of course, vary with the compound employed, the mode of administration and the treatment desired. However, in general, satisfactory results are obtained when compounds are administered at a dosage of from 0.1 to 50 mg per kg of animal weight in test set out in Example A. For man the total daily dosage is in the range of from about 1 mg to 3,500 mg which may be administered in divided doses from 1 to 6 times a day or in sustained release form. Thus dosage forms suitable for administration (by inhalation or oesphageally) comprise from about 0.17 mg to 600 mg of the compound admixed with a solid or liquid pharmaceutically acceptable diluent or carrier.

According to our invention we also provide a pharmaceutical composition comprising (preferably a minor proportion of) a compound of formula I, or a pharmaceutically acceptable derivative thereof, in combination with a pharmaceutically acceptable adjuvant, diluent or carrier. Examples of suitable adjuvants, diluents or carriers are:- for tablets and dragees; lactose, starch, talc or stearic acid; for capsules, tartaric acid or lactose; for suppositories and ointments, natural or hardened oils or waxes; for inhalation compositions, coarse lactose. For use in inhalation (and other) compositions the compounds of formula I, or the pharmaceutically acceptable derivative thereof, preferably has a fine particle size of from 0.01 to 10 microns and may if desired be used in combination with a bronchodilator, e.g. isoprenaline. The compound of fine particle size may be made, for example by grinding or milling. The compositions may also contain suitable preserving, stabilising and wetting agents, solubilisers, sweetening and colouring agents and flavourings. The compositions may, if desired, be formulated in sustained release form. Compositions for inhalation may also comprise a solution, e.g. an aqueous solution, of the compound of formula I or the pharmaceutically acceptable derivative thereof; or may comprise a mixture of the compound with a liquifyable gas, under pressure, the mixture being put up in a container having a valve adapted to dispense a metered dose.

According to our invention we also provide a process for the production of a pharmaceutically acceptable salt of a compound of formula I, which comprises treating a compound of formula I or a salt thereof, with a compound containing an available pharmaceutically acceptable cation, e.g. an appropriate base, or with an appropriate salt using a metathetical process.

As specific values of $R_1$ to $R_6$ there may be mentioned hydrogen, chlorine, hydroxy, ethyl, ethoxy, allyl, hydroxypropoxy, ethoxy-ethoxy, chloro-ethoxy and benzyl. We prefer that not more than one of $R_1$ to $R_3$ and not more than one of $R_4$ to $R_6$ are other than hydrogen. In particular we prefer that all of $R_1$ to $R_6$ are hydrogen.

X is preferably a saturated hydrocarbon group, for example an alkylene group, which is optionally substituted by an -OH group. It is also preferred that X contains 2 to 8 carbon atoms and is, for example a $—CH_2CHOHCH_2—$ or a $—CH_2CH_2CHOHCH_2CH_2—$ group. We prefer that the —OXO— group links the 5 and 5' positions on the chromone nuclei.

The invention is illustrated but in no way limited by the following Examples in which, unless otherwise stated, the parts are by weight and the temperatures are in degrees centigrade.

Example 1

5-[3-(2-Carboxy-4-oxo-4H-1-benzopyran-5-yloxy)-2-hydroxypropoxy]-4-oxo-4H-1-benzopyran-2-carbohydroxamic acid, disodium salt 1. Sodium 5-[3-(2-methoxycarbonyl-4-oxo-4H-1-benzopyran-5-yloxy)-2-hydroxypropoxy]-4-oxo-4H-1-benzopyran-2-carboxylate A solution of sodium hydroxide (0.8g) in methanol (20 ml) was added dropwise over 2 hours to a stirred suspension of diethyl 5,5'-(2-hydroxypropoxy)bis(4-oxo-4H-1-benzopyran-2-carboxylate) (10 g) in a 1:1 chloroform: methanol mixture (200 ml) at room temperature.

The resulting suspension was stirred for a further 15 minutes at room temperature and filtered. The solid was washed with chloroform and dried to give the title compound as a white solid (9.2 g), m.p. > 300°.

Spectral confirmation

The i.r. spectrum (nujol mull) contains a peak at 1740 cm$^{-1}$, due to the ester carbonyl group.

The n.m.r. spectrum (solvent d$_6$ - DMSO) shows a sharp singlet at 6.10τ due to the protons of the methyl ester group, a broadened singlet at 5.68τ due to the protons in the linking chain, two singlets at 3.41τ and 3.30τ due to the two 3-protons of the chromone rings, and multiplets in the range 2.10τ to 3.10τ due to the aromatic protons.

The mass spectrum of the free carboxylic acid derived from this compound does not show a molecular ion, but fragmentation peaks at m/e 259 and 263 due to the ester half of the molecule, and a peak at m/e 44 due to decarboxylation of the carboxylic acid half of the molecule indicate that the proposed structure is correct.

2. 5-[3-(2-Carboxy-4-oxo-4H-1-benzopyran-5-yloxy)-2-hydroxy-propoxy]-4-oxo-4H-1-benzopyran-2-carbohydroxamic acid, monosodium salt To a solution of hydroxylamine hydrochloride (7.0 g) and sodium hydroxide (4.0 g) in a 1:1 water:N,N'-dimethylformamide mixture (200 ml) was added sodium 5-[3-(2-methoxycarbonyl-4-oxo-4H-1-benzopyran-5-yloxy)-2-hydroxypropoxy]-4-oxo-4H-1-benzopyran-2-carboxylate (5.0 g), and the resulting suspension was stirred at room temperature for 24 hours.

The mixture was then filtered, and the solid was washed with ethanol and dried to give the title compound as a yellow solid (2.6 g), m.p. > 300°, which gave a positive reaction to the ferric chloride test for hydroxamic acids.

Spectral confirmation

The i.r. spectrum (nujol mull) ccontains a peak at 1700 cm$^{-1}$, due to the carbonyl group of the hydroxamic acid. It did not show an ester carbonyl peak.

The n.m.r. spectrum (solvent $d_6$ - DMSO) shows an unresolved multiplet centred at 5.71$\tau$ due to the protons in the linking chain, singlets at 3.53$\tau$ and 3.50$\tau$ due to the 3-protons of the chromone rings, multiplets in the range 2.00$\tau$ to 3.10$\tau$ due to the aromatic protons, and a broad signal centred at 6.40$\tau$, exchangeable with $D_2O$, due to the hydroxamic acid protons.

3. 5-[3-(2-Carboxy-4-oxo-4H-1-benzopyran-5-yloxy)-2-hydroxy-propoxy]-4-oxo-4H-1-benzopyran-2-carbohydroxamic acid, disodium salt 5-[3-(2-Carboxy-4-oxo-4H-1-benzopyran-5-yloxy)-2-hydroxy-propoxy]-4-oxo-4H-1-benzopyran-2-carbohydroxamic acid mono-sodium salt (505 mg) was dissolved in a solution of sodium bicarbonate (84 mg) in water (35 ml). The solution was filtered and concentrated by azeotropic distillation with iso-propanol until the product began to precipitate from solution. The mixture was filtered, and the solid was washed with aqueous iso-propanol and dried to give the title compound as a buff solid (257 mg), m.p. > 300°. (C 44.14%, H 3.7%, N 2.3%; $C_{23}H_{15}NNa_2O_{11}.5½ H_2O$ requires C 44.14%, H 4.1%, N 2.2%).

Spectral confirmation

The i.r. spectrum (KBr disc) does not contain any carbonyl peaks in the 1700 cm$^{-1}$ region.

The n.m.r. spectrum (solvent $d_6$ - DMSO) shows a broadened singlet centred at 5.69$\tau$ due to the protons in the linking chain, two singlets at 3.55$\tau$ and 3.48$\tau$ due to the two 3-protons of the chromone rings, and multiplets in the range 2.00$\tau$ to 3.10$\tau$ due to the aromatic protons.

EXAMPLE 2

The following compounds, and their di-sodium salts, may be made by one or more of the processes described above:

a. 5-[3-(2-(tetrazol-5-yl)-4-oxo-4H-1-benzopyran-5-yloxy)-2-hydroxypropoxy]-4-oxo-4H-1-benzopyran-2-carbohydroxamic acid.

b. 6-[8-(2-(tetrazol-5-yl)-4-oxo-4H-1-benzopyran-6-yloxy)-octanyloxy]-8-chloro-4-oxo-4H-1-benzopyran-2-carbohydroxamic acid.

c. 7-[3-(2-(tetrazol-5-yl)-4-oxo-4H-1-benzopyran-7-yloxy)-2-hydroxypropoxy]-6-hydroxy-4-oxo-4H-1-benzopyran-2-carbohydroxamic acid.

d. 8-[3-(2-(tetrazol-5-yl)-4-oxo-4H-1-benzopyran-8-yloxy-2-hydroxypropoxy]-6-ethyl-4-oxo-4H-1-benzopyran-2-carbohydroxamic acid.

e. 5-[8-(2-(tetrazol-5-yl)-4-oxo-4H-1-benzopyran-5-yloxy)-4-oxaoctanyloxy]-8-ethoxy-4-oxo-4H-1-benzopyran-2-carbohydroxamic acid.

f. 5-[3-(2-(tetrazol-5-yl)-4-oxo-4H-1-benzopyran-5-yloxy-2-hydroxypropoxy]-8-allyl-4-oxo-4H-1-benzopyran-2-carbohydroxamic acid.

g. 5-[3-(2-(tetrazol-5-yl)-4-oxo-4H-1-benzopyran-5-yloxy)-2-hydroxypropoxy]-7-(ethoxy-ethoxy)-4-oxo-4H-1-benzopyran-2-carbohydroxamic acid.

h. 7-[3-(2-(tetrazol-5-yl)-4-oxo-4H-1-benzopyran-7-yloxy)-2-hydroxypropoxy]-5-hydroxypropoxy-4-oxo-4H-1-benzopyran-2-carbohydroxamic acid.

i. 7-[3-(2-(tetrazol-5-yl)-4-oxo-4H-1-benzopyran-7-yloxy)-2-hydroxypropoxy]-5-chloroethoxy-4-oxo-4H-1-benzopyran-2-carbohydroxamic acid.

j. 5-[3-(2-(tetrazol-5-yl)-4-oxo-4H-1-benzopyran-5-yloxy)-2-hydroxypropoxy]-6-benzyl-4-oxo-4H-1-benzopyran-2-carbohydroxamic acid.

EXAMPLE A

The procedure set out below may be used to assess the effectiveness of a compound in inhibiting the release of the pharmacological mediators of anaphylaxis.

In this test, the effectiveness of the compounds in inhibiting the passive cutaneous anaphylactic reaction in rats is assessed. It has been proved that this form of test gives reliable qualitative indications of the ability of the compounds under test to inhibit antibody-antigen reaction in man.

In the test method Charles River France/Fisons bred rats (male or female) having a body weight of from 100 to 150 gms are infected subcutaneously at weekly intervals with N. brasiliensis 1 larvae in doses increasing from about 2000 larvae per animal to 12000 larvae per animal in order to establish the infection. After 8 weeks the rats are bled by heart puncture and 15–20 mls. of blood collected from each animal. The blood samples are then centrifuged at 3500 rpm. for 30 minutes in order to remove the blood cells from the blood plasma. The serum is collected and used to provide a serum containing N. brasiliensis antibody. A pilot sensitivity test is carried out to determine the least quantity of serum required to give a skin weal in control animals in the test described below of 2 cm diameter. It has been found that optimum sensitivity of rats in the body weight range 100–130 gms is obtained using a serum diluted with eight parts of physiological saline solution. This diluted solution is called antibody serum A.

The anitgen to react with the anitbody in serum A is prepared by removing N. brasiliensis worms from the gut of the infested rats, centrifuging the homogenate and collecting the supernatant liquor. This liquor is diluted with saline to give a protein content of 1 mg/ml and is known as solution B.

Charles River France/Fisons Bred rats in the body weight range 100 to 130 gms are sensitised by intra dermal injection of 0.1 mls of serum A into the right flank. Sensitivity is allowed to develop for 24 hours and the rats are then injected intravenously with 1 ml/100 gms body weight of a mixture of solution B (0.25mls), Evans Blue dye solution (0.25 mls) and the solution of the compound under test (0.5 mls varying percentages of active matter). Insoluble compounds are administered as a separate intraperitoneal injection 5 minutes before intravenous administration of solution B and Evans Blue dye. For each percentage level of active matter in the solution under test five rats are injected. Five rats are used as controls in each test. The dosages of the compound under test are selected as to give a range of inhibition values.

Thirty minutes after injection of solution B the rats are killed and the skins removed and reversed. The intensity of the anaphylactic reaction is assessed by comparing the size of the characteristic blue weal produced by spread of the Evans Blue dye from the sensitisation site, with the size of the weal in the control animals. The size of the weal is rated as 0 (no weal detected, i.e. 100% inhibition) to 4 (no difference in size of weal, i.e. no inhibition) and the percentage inhibition for each dose level calculated as:

$$\% \text{ inhibition} = \frac{(\text{Control group score} - \text{treated group score})}{\text{Control group score}} \times 100$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal and gastric administration of the compound.

We claim:
1. A compound of formula I,

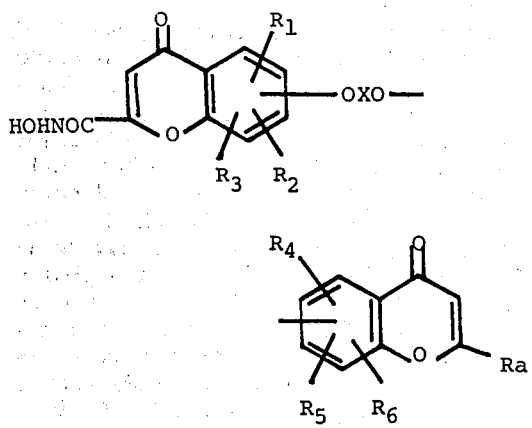

in which
$R_1$, $R_2$, $R_3$, $R_4$, $R_5$ and $R_6$, which may be the same or different, each represent hydrogen, halogen, hydroxy, alkyl of 1 to 6 carbon atoms, alkoxy of one to six carbon atoms, alkenyl of up to six carbon atoms; the alkyl and alkoxy groups being unsubstituted or substituted by hydroxy, alkoxy of 1 to 6 carbon atoms, halogen or phenyl and X is an alkylene containing from 2 to 10 carbon atoms which is unsubstituted or is substituted with an OH group, or an alkylene group containing from 2 to 10 carbon atoms which is interrupted by an oxygen atom, and which is otherwise unsubstituted or is substituted by an —OH group, Ra is —COOH, or 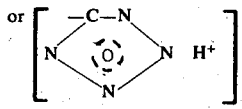

or a pharmaceutically acceptable salt thereof.

2. A compound according to claim 1, wherein $R_1$ to $R_6$ are selected from hydrogen, chlorine, hydroxy, ethyl, ethoxy, allyl, hydroxy-propoxy, ethoxy-ethoxy, chloro-ethoxy and benzyl.

3. A compound according to claim 1, wherein not more than one of $R_1$ to $R_3$ and not more than one of $R_4$ to $R_6$ are other than hydrogen.

4. A compound according to claim 1, wherein all of $R_1$ to $R_6$ are hydrogen.

5. A compound according to claim 1, wherein X is an alkylene group which is unsubstituted or is substituted by an -OH group.

6. A compound according to claim 1, wherein X contains from 2 to 8 carbon atoms.

7. A compound according to claim 1, wherein X is a —CH$_2$CHOHCH$_2$— or a —CH$_2$CH$_2$CHOHCH$_2$CH$_2$— group.

8. A compound according to claim 1, wherein the —OXO— group links the 5 and 5' positions on the chromone nuclei.

9. A compound according to claim 1 which is 5-[3-(2-carboxy-4-oxo-4H-1-benzopyran-5-yloxy)-2-hyxroxypropoxy]-4-oxo-4H-1-benzopyran-2-carbohydroxamic acid, or a pharmaceutically acceptable salt thereof.

10. A compound according to claim 1 having a particle size of frrom 0.01 to 10 microns.

* * * * *